United States Patent [19]

Thompson

[11] 4,301,793
[45] Nov. 24, 1981

[54] SIGH PRODUCING MECHANISM FOR POSITIVE PRESSURE RESPIRATOR

[76] Inventor: Harris S. Thompson, 175 Bellevue Dr., Boulder, Colo. 80302

[21] Appl. No.: 93,794

[22] Filed: Nov. 13, 1979

[51] Int. Cl.³ .............................................. A61M 16/00
[52] U.S. Cl. ........................... 128/204.21; 128/205.24
[58] Field of Search ...................... 128/204.21, 204.23, 128/205.15, 205.24, 203.14, 200.18, 200.21, 205.18, 204.18, 203.12, 204.25, 204.24, 205.13, 205.14; 415/51, 125

[56] References Cited

U.S. PATENT DOCUMENTS

| | | | |
|---|---|---|---|
| Re. 29,778 | 9/1978 | Stewart | 128/204.24 |
| 3,863,630 | 2/1975 | Cavallo | 128/204.21 |
| 3,910,270 | 10/1975 | Stewart | 128/204.24 |

*Primary Examiner*—Henry J. Recla
*Attorney, Agent, or Firm*—Jerry W. Berkstresser; Dennis K. Shelton; Bruce G. Klaas

[57] ABSTRACT

A sigh producing mechanism in a blower type positive pressure respirator. In breathing, a normal person will occasionally take a deep breath, a sigh, to break the monotony of regular breathing. In artificial respiration, such occasional sighs are also desired. The sigh is produced by an increase in the speed of the blower for a few breathing cycles. To produce the sigh, the resistance to the blower motor is reduced and this is accomplished with the aid of a timer to space the sigh intervals and limit the duration of the sigh cycles.

5 Claims, 5 Drawing Figures

SIGH PRODUCING MECHANISM FOR POSITIVE PRESSURE RESPIRATOR

The present invention relates to positive pressure respiration apparatus, and more particularly to portable, blower-type positive pressure respiration apparatus. Such apparatus is disclosed in my U.S. Pat. No. 3,094,274. The primary object of the present invention is to provide for occasional controlled sigh cycles when a patient is using the respiration apparatus.

In normal use, the blower of a portable positive pressure respiration apparatus runs continuously, and a cyclic control valve operates at a selected breathing rate to direct a pressurized airflow to a patient through a breathing tube during the inspiration cycle and to divert and exhaust the airflow during the expiration cycle. This exhaust of air occurs when the patient expires air at atmospheric pressure using his normal reflexes to do so. The pressure build-up pattern of an air flow to the patient during the inspiration cycle is established by the shape of the ports in the cyclic control valve and the maximum pressure to which the patient will be subjected is established by the speed of the blower. A rheostat speed control and a pressure gauge are used with the apparatus to select and establish this maximum pressure. Other modes for controlling this maximum pressure, such as relief valves, are not generally used because operation of the blower at a higher-than-necessary-pressure wastes energy, an important factor when a portable respiration apparatus is being operated with a storage battery away from a 110 volt A.C. power source.

It has been established that many patients will favorably respond to occasional variations in pressure and the volume of air pumped into their lungs during breathing cycles. For example, an occasional deep breath, or 'sigh' is quite desirable. This is discussed in an article entitled "Prolonged Alteration of Lung Mechanics in Kyphoscoliosis by Positive Pressure Hyperinflation" by R. Sinha and E. H. Bergofsky, American Review of Respiratory Disease, Volume 106, 1972, at page 72.

In clinics and hospitals where piston or pump type artificial respiration apparatus is available, it is a common practice to extend the stroke of the piston, or its equivalent, and use a valving system which permits only a portion of the volume of piston displacement for normal breathing and a greater amount whenever a "sigh" is desired. With such apparatus, in clinics and hospitals, electrical energy to drive the apparatus is available and efficiency in that regard is not a factor.

It appeared that with the blower-type apparatus such sighs, increases of pressure and volume of air during a breathing cycle were not practical because the pressure was limited by the speed of the blower. There is, nevertheless, a need and demand for providing a 'sigh' feature in a portable positive pressure respiration apparatus, without changing its normal mode of operation.

The present invention was conceived and developed with the foregoing and other considerations in view and comprises, in essence, a control circuit mechanism in the apparatus to increase the speed of the blower for a few breathing cycles at selected time intervals, say, for example, once an hour, to produce a 'sigh' for a few breathing cycles which will alter the monotonous uniform breathing action of the apparatus.

Other objects of the invention are to provide a novel and improved blower-type positive pressure respiration apparatus having the capability of producing a 'sigh' action at a selected pressure increase and at selected intervals of time which: (a) does not require any changes in the design of existing positive pressure breathing apparatus units, and is merely a simple addition thereto, (b) requires only a few, simple, compact circuit components which may be easily incorporated into existing apparatus, (c) is easily adjustable and can be adjusted to any desired sigh pressure, sustained time interval, and any desired time lapse between sighs, (d) can, if desired, be easily adjusted to change the length of time of the inspiration-expiration cycles to emulate a breath-holding action which occurs when a normal person takes a deep breath, or sigh, (e) does not consume any significant excess of power when in use; and (f) is a neat, economical array of components which does not significantly increase the cost of a positive pressure respirator.

With the foregoing and other objects in view, my invention comprises certain constructions, combinations and arrangements of parts and elements as hereinafter described, defined in the appended claims and illustrated in the accompanying drawing in which:

Figure 1:
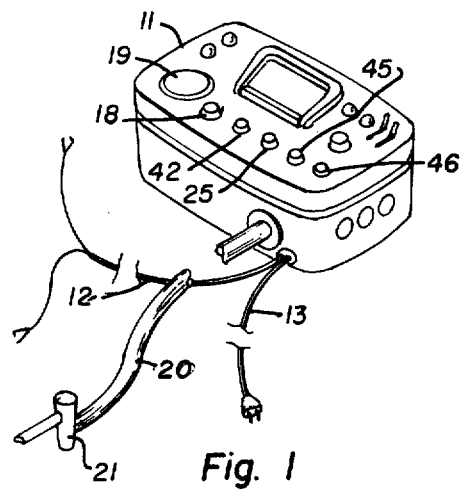
FIG. 1 is an isometric view of the case of a portable positive pressure respiration apparatus showing a breathing tube and electrical leads which are partially broken away to conserve space.
Figure 2:
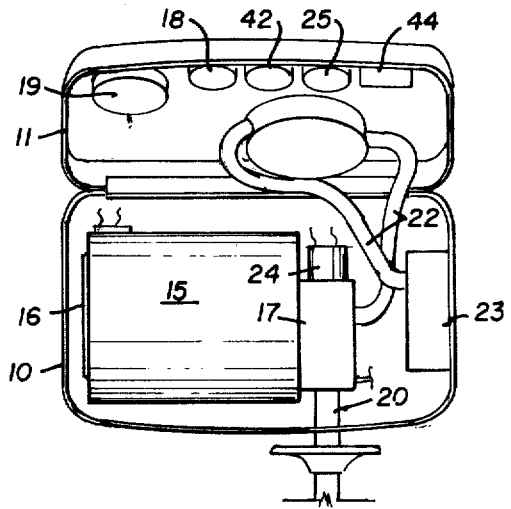
FIG. 2 is a plan view of the case of FIG. 1 with the top being opened to show the components therewithin; however only those components which aid in the understanding of the present invention are shown.

Referring more particularly to the drawing, a portable blower-type positive-pressure respiration apparatus is ordinarily carried in a case 10 which is closed by a lid 11. In the model depicted, several controls and pressure and light indicators are shown on the lid 11, as hereinafter further described. An electrical cord 12 for connection with a battery is supplemented by a second electrical cord 13 for the receptacle of a 110-volt A.C. power source. A suitable transformer and rectifier, not shown, may be installed within the case to provide for a 12-volt D.C. power supply regardless of the power source used.

A cylindrical blower unit 15 within the case has an intake end 16 at one side of the unit and the opposing discharge end is connected to a breathing cycle control valve 17. The components within the cylindrical blower 15, include the intake filters, an electrical drive motor and an air turbine. Except for a portion of the drive motor shown in broken lines, these components are not shown since they are conventional. A manually adjustable rheostat control 18 is located on the lid 11 as shown at FIG. 1. The control 18 regulates the speed of the blower and thereby the pressure of air delivered to a patient. A pressure gauge 19, indicating the discharge pressure, is also located on the lid 11 of the case.

The cycle control valve 17, connecting with the discharge end of the blower 15 connects with a breathing tube 20 and extends a suitable distance from the apparatus to terminate as a mouthpiece 21 for use by a patient. The pressure gauge 19 measures pressure in this breathing tube 20 and is connected thereto by a lead not shown. The cycle control valve 17 also has a discharge line 22 which will exhaust to the atmosphere, as through a muffler 23 after the discharge airflow is used for cooling resistor components in the system. A drive motor 24 operates the cycle control valve 17 at a selected rate and a manually adjustable rheostat control 25 is mounted on the lid 11 to regulate the speed of this motor 24 to provide for a selected rate of breathing by a patient, for example, twenty breaths per minute.

Figure 3:
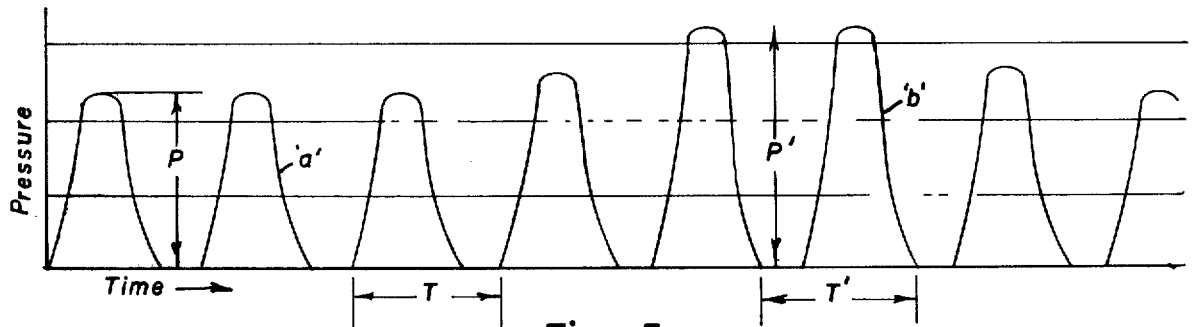
FIG. 3 is an exemplary pressure-time curve as can be produced by the apparatus, to show both regular breathing cycles and also sigh cycles of increased pressure.

A typical breathing pattern is illustrated by the cyclic curves 'a' at FIG. 3. To modify this apparatus to produce a 'sigh,' as shown by the curves 'b' at FIG. 3, it is necessary to provide two additional controls: a first control to speed up the blower to establish the increased pressure of the 'sigh;' and a second control to initiate the sigh, at a specified time interval for actuating the sigh and also the sigh duration. For example, the 'sigh' may be actuated once an hour and last for six seconds. The present invention accomplishes these functions by the use of simple supplemental circuits without disturbing the conventional circuits in the apparatus. It is to be noted that the speed of the blower 15, which produces the pressure in the breathing tube 20, is controlled by varying the voltage at the blower motor.

Figure 4:
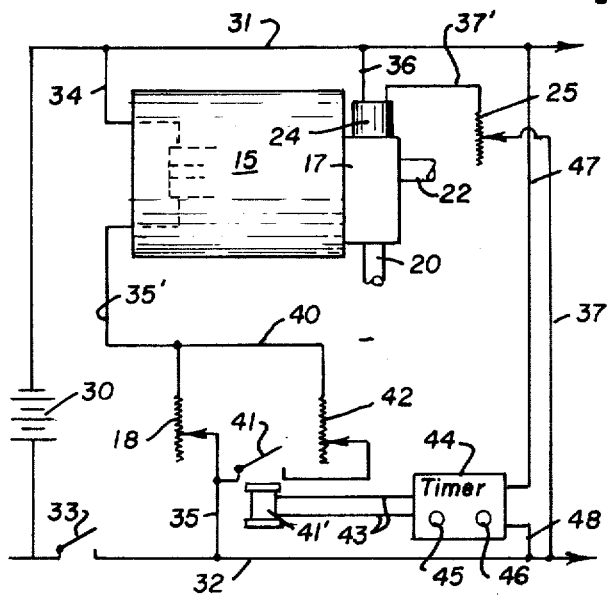
FIG. 4 is a circuit diagram of some of the circuits in the positive pressure respiration apparatus shown at FIG. 1 including the circuits and components necessary to produce a 'sigh'.

Referring to FIG. 4, the apparatus, including the blower 15, is operated by a battery 30 or an equivalent power source. Positive and negative main leads 31 and 32 extend from the battery to the several components of the apparatus. A manually-operated master switch 33 in lead 32 is closed to turn on the apparatus. A branch 34 extends from lead 31 to one side of the motor of blower 15 and a branch 35 extends from lead 32 to the adjustable rheostat 18 and thence, as branch 35' to the other side of the blower motor. When the master switch 33 is closed, this conventional arrangement permits the motor of the blower 15 to operate and the setting of rheostat 18 controls the voltage and the speed of the motor of blower 15, and therefore, the resulting pressure in the breathing tube 20.

A branch 36 also extends from the main lead 31 to one side of the drive motor 24 of the cycle control valve 17 and a branch 37 extends from the lead 32 to the adjustable rheostat 25 and thence, as branch 37' to the other side of the drive motor 24. When the master switch 33 is closed, this conventional arrangement permits the drive motor 24 of the cycle contol valve to operate and the setting of the rheostat 25 establishes a desired speed of the control valve to time the inspiration-expiration breathing cycle to any selected duration interval T, indicated at FIG. 3.

The apparatus above described produces inspiration and expiration breathing cycles having a pressure P and a duration T as shown by the inspiration-expiration curves 'a' at FIG. 3. The shape of these curves is established by the shape of the ports in the valve 17 and may vary from that shown at FIG. 3. In accordance with the present invention, a 'sigh' is produced by an increased pressure P', as shown by the curves 'b' at FIG. 3, and to do so, it is necessary to increase the speed of the blower motor. The speed of the blower is governed by the voltage across lead branches 34 and 35'. This voltage is controlled by the resistance of rheostat 18. To reduce this resistance to increase the speed of the blower, a lead branch 40 shunts the rheostat 18 connecting with the leads 35-35'. This lead branch 40 includes a normally open relay switch 41 and a manually adjustable rheostat control 42. Accordingly, whenever the relay switch 41 closes, the resistance of the leads is reduced and the adjustment of rheostat 42 establishes a suitable pressure P'.

For a sigh, it is desirable that the relay switch 41 close at time intervals which may be a lapse time of an hour or more and remain closed for only a short, sustained time, a few seconds, so that only two or three inspiration-expiration breathing cycles occur at the elevated pressure P'. The relay coil 41' is energized through leads 43 which connect to a double-action timer 44. The timer 44 has a first adjustment 45 for the lapse time and a second adjustment 46 for the sustained time. To energize this timer 44, it will be connected to the main leads 31 and 32 by branches 47 and 48.

The timer 44 may be obtained as a conventional electronic or mechanical unit, for example, General Time Company of Thomaston, Conn., solid state timer Series 2113, and Eagle Signal Co. of Davenport, Iowa, Flex-opulse repeat cycle timer No. 320, are suitable units since both the lapse time and the sustain time adjustments are manual. The timer 44 and dials for adjustments 45 and 46 may be mounted in the lid 11 as indicated at FIG. 1 or the timer 44 may be located within the case since its adjustments will not be changed very often. A fixed timer can also be made as an R.C. circuit, when it is desirable to set the time intervals at the factory and eliminate the adjustment feature. R.C. circuits for lapse time and sustained time are well within the skill of a designer, and such a device is shown in the Semi-Conductor Data Library, Series A, Volume VI, published by Motorola, Inc., (1975 Edition) Section 8, p. 302. Hence, such need not be described in detail.

It is to be noted that circuits differing from the circuits herein described, but fully equivalent thereto, are easily possible. The above described circuits can even be simplified by incorporating a timer in the branch lead 40 in lieu of the relay switch 41 if the timer can operate at the current which passes through lead 40. Another alternative is to use a two-way switch instead of switch 41 to cut out the rheostat 18 when the switch closes to cut in rheostat 42. Such alternates need not be described since a skilled engineer can easily design and build such alternate arrangements with the aid of the disclosure set forth above.

As a further refinement to the present invention, the time of an inspiration-expiration duration cycle T can be increased during the increased pressure sigh period, as indicated by T' at FIG. 3. This simulates a common breathing action for whenever a normal person takes a deep breath, a sigh, he will ordinarily do so at a slower breathing rate. In using a positive pressure breathing apparatus, the desired result, an increased inspiration-expiration duration cycle time T', can be obtained by slowing down the drive motor 24 of the cycle valve 17.

Figure 5:
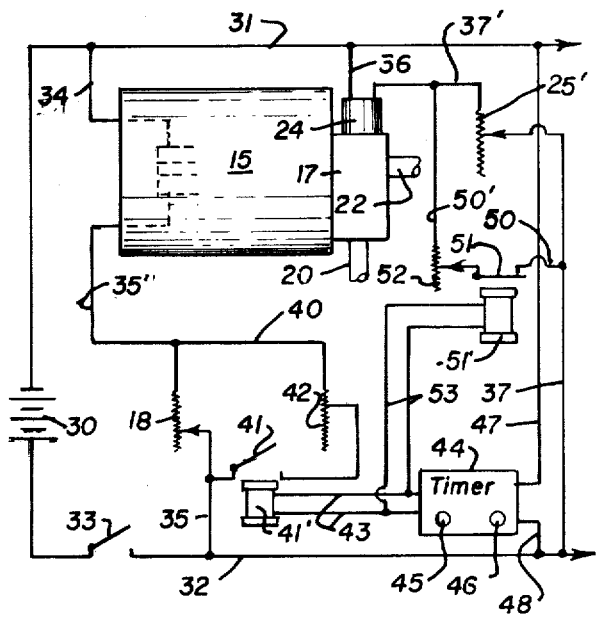
FIG. 5 is a partial circuit diagram similar to FIG. 4, but with a modification to increase the time of the inspiration-expiration cycles of breathing, as well as the pressure, during a sigh.

FIG. 5 is a circuit diagram essentially identical to the circuit diagram of FIG. 4 to show that only slight modifications are required to accomplish this desired result. To slow down the drive motor 24 it is necessary to increase the resistance in the connecting lead branch 37-37'. One mode of accomplishing this is to shunt the rheostat 25 in the branch 37-37' by a branch 50-50' which includes a normally closed relay switch 51 and a rheostat 52. In normal operation, the resistance through the parallel-connected rheostats 25 and 51 is adjusted to cause the drive motor 24 to rotate the cycle valve 17 at a rate which porduces the regular time interval T. When the normally closed relay switch 51 opens, the voltage at the drive motor 24 is reduced and the motor slows down to produce the longer time interval T'. Adjustments must be first to rheostat 25 with the relay switch 51 open to obtain the interval T', and then to rheostat 52 with the relay switch 51 closed to obtain the time interval T.

The switch 51 is opened by its relay coil 51' which is connected to the timer 44 by leads 53 connecting with leads 43. Thus, the sigh action produced when the timer acts then causes both the pressure P' in the breathing tube and the cycle time interval T' to be increased.

I have now described my invention in considerable detail; however, it is obvious that others skilled in the art can devise and build alternate and equivalent constructions which are within the spirit and scope of the invention. Hence, I desire that my protection be limited, not by the constructions illustrated and described, but only by the scope of the appended claims.

What is claimed is:

1. A positive pressure breathing apparatus having:
 a blower having an electrically operated blower motor controlled by a blower drive circuit and an intake and a discharge;
 a cyclic valve having at least one inlet and at least one outlet said inlet being in fluid communication with the discharge of said blower; and means for controlling of said cyclic valve in a timed manner according to inhalation and exhalation phases fluid communication between said inlet and said outlet;
 a breathing tube in fluid communication with the outlet of said cyclic valve, provided with means for exhausting air to produce an expiration cycle; and
 means for controlling the pressure output of said blower operatively associated with the blower motor to controllably produce a preselected air pressure in said breathing tube, said pressure control means includes a means in the blower drive circuit for changing motor speed, the improvement comprising:
 (a) a supplementary control means including a circuit shunting said motor speed changing means to increase the speed of the blower motor and thereby, the pressure at the breathing tube whenever the supplementary control means is activated; and
 (b) timer means adapted to activate the supplementary control means after a lapse time period sufficient to provide a large number of inspiration cycles at regular pressure and to continue such activation for a short sustained time period sufficient to provide a small number of inspiration cycles at increased pressure to produce a small number of sigh breaths in the breathing pattern of the respirator between lapse time periods.

2. The apparatus defined in claim 1 wherein:
 (a) the supplementary control means includes a shunting circuit and a rheostat and a normally open shunt switch electrically connective to said rheostat; and
 (b) the timer means includes a switch closing means adapted to close said normally open shunt switch during the aforesaid sustained time period; and
 (c) timer control means.

3. The apparatus defined in claim 2, wherein the blower includes:
 (a) the pressure control means includes a blower motor drive circuit which drives the motor at a speed related to the voltage in the driver circuit at the motor, and a rheostat in the drive circuit to vary the voltage and to impose a selected voltage at the motor;
 (b) the supplementary control means includes a supplementary rheostat in this shunting circuit electrically connected to said normally open shunt switch, whereby closing of the shunt switch increases the voltage at the motor; and the timer means includes a relay coil electrically connected to open said shunt switch when said relay is energized and means to energize the timer control means during the sustained time period.

4. The apparatus defined in claim 3 including:
 (a) an electrical cyclic motor to drive the cyclic valve;
 (b) a cyclic driver circuit to drive the cyclic motor at a speed related to the voltage at the cyclic motor and a rheostat in the cyclic driver circuit;
 (c) a supplementary cyclic control circuit shunting the rheostat in the cyclic driver circuit, said control circuit including a supplementary rheostat and a normally closed relay switch; and,
 (d) the coil of the relay switch is connected with the aforesaid timer control circuit whereby to open said normally closed switch whenever the timer control circuit is energized, to thereby slow down the cyclic motor.

5. The apparatus defined in claim 1, including:
 (a) a cyclic control means adapted to regulate the inspiration-expiration rate of the cyclic valve;
 (b) a supplementary cyclic control means associated with the cyclic control means to slow down the inspiration-expiration rate whenever the supplementary cyclic control means is activated;
 (c) means associated with the timer means adapted to activate the supplementary cyclic control means during the aforesaid sustained time period, whereby to increase the length of time between the said sigh breaths;
 (d) the supplementary cyclic control means is an electric motor, a driver circuit to the motor and a rheostat in the circuit to vary the voltage at and speed of the motor by imposing a resistance in the circuit; and
 (e) the supplementary cyclic control means includes a means to increase the resistance of said circuit to controllably change the speed of the motor.

* * * * *